United States Patent
Shields et al.

(10) Patent No.: US 6,340,781 B1
(45) Date of Patent: *Jan. 22, 2002

(54) PURIFICATION OF PENTAFLUOROETHANE

(75) Inventors: Charles John Shields, Warrington; Gary Goodyear, Wirral, both of (GB)

(73) Assignee: Imperial Chemical Industries PLC, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 08/374,669

(22) PCT Filed: Jul. 20, 1993

(86) PCT No.: PCT/GB93/01518

§ 371 Date: Apr. 3, 1995

§ 102(e) Date: Apr. 3, 1995

(87) PCT Pub. No.: WO94/02439

PCT Pub. Date: Feb. 3, 1994

(30) Foreign Application Priority Data

Jul. 22, 1992 (GB) ............................................. 9215562
Jul. 22, 1992 (GB) ............................................. 9215563

(51) Int. Cl.$^7$ ............................................. C07C 17/395
(52) U.S. Cl. ........................................ 570/177; 570/178
(58) Field of Search ................................ 570/177, 117, 570/178

(56) References Cited

U.S. PATENT DOCUMENTS 5,001,287 A  *  3/1991   Fernandez et al. ........... 570/178

FOREIGN PATENT DOCUMENTS

WO          90 8750         8/1990

OTHER PUBLICATIONS

Chemical Abstracts, vol. 117, No. 11, Sep. 14, 1992, abstract No. 111124x. Hiromo Ono et al:, "Purification of 1,1,1,2–tetrafluoroethane", p. 815; col. 2; JP,A,0489 437, Mar. 23, 1992.

Chemical Abstracts, vol. 116, No. 25, Jun. 22, 1992, abstract No. 255164n, Shinsuke Morikawa, et al: "Preparation of pentafluoroethane", p. 745; col. 1., JP A,) 429 941, Jan. 31, 1992.

* cited by examiner

Primary Examiner—Alan L. Rotman
Assistant Examiner—Rita Desai
(74) Attorney, Agent, or Firm—Pillsbury Winthrop LLP

(57) ABSTRACT

A process for the removal of chloroalkane, chlorofluoroalkane and/or hydrofluoroalkane impurities from pentafluoroethane which comprises contacting the impure pentafluoroethane with hydrogen at elevated temperature in the presence of a hydrogenation catalyst to convert the impurity or impurities to a hydrofluoroalkane and/or a hydrocarbon and separating the resulting hydrofluoroalkane and/or hydrocarbon from the pentafluoroethane.

8 Claims, No Drawings

PURIFICATION OF PENTAFLUOROETHANE

This invention relates to a process for the purification of pentafluoroethane and in particular to a process for the removal of chlorine-containing impurities and/or hydrofluoroalkane impurities from compositions containing pentafluoroethane.

Recently, processes have been proposed for the production of pentafluoroethane which has been proposed, together with other hydrofluoroalkanes such as 1,1,1,2-tetrafluoroetane, difluoromethane and 1,1,1-trifluoroethane, and blends thereof as a suitable replacement for chlorofluorocarbons due to the zero ozone depleting potential of hydrofluoroalkanes.

Thus it has been proposed in Japanese Patent Application Nos Kokai 3099026, 1258632 and 4029941 to produce pentafluoroethane by contacting pentafluorochloroethane with hydrogen in the presence of a hydrogenation catalyst. Suitable conditions of temperature and pressure and suitable catalysts are described in the aforementioned Japanese patent applications. However, these and other processes for the production of pentafluoroethane result in a product comprising pentafluoroethane together with impurities such as unconverted starting material and by-products.

Many of these impurities may be difficult to separate from pentafluoroethane by conventional processes, for example distillation, due to the similarity in boiling point between the impurity and pentafluoroethane, and/or the formation of pentafluoroethane/impurity azeotropes.

We have now found a simple process for the removal of such impurities from pentafluoroethane, by converting the impurities to a hydrofluoroalkane and/or hydrocarbon which is easily separable from pentafluoroethane.

According to the present invention there is provided a process for the removal of chlorine-containing impurities and/or hydrofluoroalkane impurities from pentafluoroethane which comprises contacting the impure pentafluoroethane with hydrogen at elevated temperature in the presence of a hydrogenation catalyst to convert the impurity of impurities to a hydrofluoroalkane and/or a hydrocarbon.

The process may be operated so as to remove chlorine-containing impurities from the pentafluoroethane to the extent that the composition recovered after the process contains less than 1% by volume of chlorine-containing impurities, preferably less than 0.5%, more preferably less than 0.1% and especially less than 0.01% of chlorine-containing impurities. Similarly the process may be operated to remove hyrofluoroethane impurities to below the level of 1% by volume.

The chlorine-containing impurity present in the pentafluoroethane will typically be a hydrochlorocarbon, chlorofluorocarbon or hydrochlorofluorocarbon. Under suitable conditions of temperature and pressure, these impurities may be converted to pentafluoroethane and/or another hydrofluoroalkane and/or hydrocarbons, for example methane and ethane which are readily separated from pentafluoroethane by conventional processes, for example distillation. Hydrofluoroalkane impurities in the pentafluoroethane will typically be converted to hydrocarbons.

In certain circumstances, and in particular where the product of hydrogenation of the impurity is itself a hydrofluoroalkane, for example 1-chloro-1,2,2,2-tetrafluoroethane which is hydrogenated to 1,1,1,2-tetrafluoroethane, the final product may itself be a desirable mixture of hydrofluoroalkanes. Furthermore the chlorine-containing impurity, chloropentafluoroethane may be hydrogenated to pentafluoroethane itself. Alternatively, it may be desirable to separate the product of hydrogenation of the impurity from the pentafluoroethane, as for example where the product of hydrogenation is a hydrocarbon or where the product of hydrogenation is a hydrofluoroalkane which is not desired as a mixture with pentafluoroethane, for example fluoromethane and fluoroethane which are the hydrogenation products of trichlorofluoromethane and dichlorofluoroethane respectively.

According to a preferred embodiment of the invention there is provided a process for the removal of chlorine-containing impurities and/or hydrofluoroalkane impurities from compositions comprising pentafluoroethane which comprises contacting the impure pantafluoroethane with hydrogen at elevated temperature in the presence of a hydrogenation catalyst to convert the impurities to a hydrofluoroalkane and/or a hydrocarbon and separating the hydrocarbon and/or hydrofluoroalkane from the pentafluoroethane.

The pentafluoroethane compositions which are treated according to the invention typically comprise major proportions of pentafluoroethane and minor proportions of chlorine-containing compounds and other hydrofluoroalkanes although compositions comprising major proportions of hydrofluoroalkanes other than pentafluoroethane may be treated according to the invention. Generally the composition treated according to the invention will comprises at least 10% by volume of pentafluoroethane and usually it will comprise at least 30% of pentafluoroethane.

The composition treated according to the invention may also comprise hydrofluoroalkanes other than pentafluoroethane. Depending upon the particular hydrofluoroalkane. the particular catalyst employed and the conditions under which the process is carried out, these hydrofluoroalkanes may be converted to hydrocarbons or to other hydrofluoroalkanes or the hydrofluoroalkanes may pass unconverted through the process of the invention.

Hydrogenation catalysts are well known in the art and a variety have been proposed, for example as described in the aforementioned Japanese patent applications. Such catalysts typically comprise a Group VIIIa metal, for example nickel, rhodium, iridium, ruthenium, palladium or platinum or a salt, for example halide or oxide, of the metal. The preferred catalyst depends to some extent upon the particular impurities present and upon the conditions of temperature and pressure employed, but in general a preferred catalyst comprises palladium, platinum and/or nickel. Such preferred catalysts may comprise only these metals or may comprise one or more of these metals and other metals which may be present as alloys with nickel. platinum and/or palladium or as mixtures of metals.

The metal catalyst is typically carried on a suitable support, for example alumina, fluorinated alumina or an active carbon.

Any of these proposed hydrogenation catalysts may be employed in the process of the invention.

Suitable conditions of temperatures and pressure under which the impurities are converted to hydrofluoroalkanes and/or hydrocarbons will depend to some extent upon the nature and amount of impurities present and the particular catalyst employed. Generally however, the temperature will be at least 350° C. and preferably at least 400° C. The temperature is usually not higher than 600° C. and preferably will not be higher than about 500° C. More preferred temperatures are in the range from about 420° C. to about 520°.

The process may be carried out under atmospheric pressure, although we prefer to employ superatmospheric pressures. say up to about 30 bar. and preferably superatmospheric pressures in the range from about 5 bar to about 25 bar.

The amount of hydrogen employed in the process may vary within wide limits and is dependent to some extent upon the amount and nature of the chlorine-containing impurities and/or hydrofluoroalkane impurities which may be hydrogenated in the process of the invention. Generally we prefer to use at least a stoichiometric excess of hydrogen based on the impurity or impurities to be hydrogenated and more preferably a stoichiometric excess in the range of from 1:1 to about 10:1, more preferably from about 2:1 to about 8:1.

The invention is illustrated but not limited by the following examples.

EXAMPLE 1

87 ml of a catalyst comprising 16.0% nickel oxide supported on alumina was charged to a one inch diametre Monel reactor tube, the tube was placed in an oven and the catalyst was dried by heating to 250° C. in a stream of nitrogen (100 ml/minute) for 16 hours.

The nitrogen flow rate was increased to 3000 ml/minute and a stream of hydrogen was passed over the catalyst at a flow rate of 120 ml/minute. A mixed organic feed stream comprising 1.1,1-trifluoroethane. pentafluoroethane. 1,1,1,2-tetrafluoroethane and chloropentafluoroethane in the proportions shown in Table 1 was passed over the catalyst at atmospheric pressure and 400° C. The off gases were analysed by gas chromatography and the results are shown in Table 1.

TABLE 1

| SAMPLE | TEMP (° C.) | $H_2$/Org Ratio | COMPOSITION (gc area %) | | | | |
|---|---|---|---|---|---|---|---|
| | | | 143a | 125 | 134a | 115 | ethane/methane |
| Feed | — | — | 57.6 | 8.8 | 33.2 | 0.1 | 0.0 |
| Off Gas | 400 | 8:1 | 0.0 | 11.5 | 25.7 | 0.0 | 37.3 |

EXAMPLE 2

31 g of a catalyst comprising 16% nickel oxide supported on alumina was charged to a ¾" Inconel reactor tube and the reactor tube was placed in an oven. Hydrogen (0.057 g/minute) and a mixed organic stream comprising 1,1,1-tetrafluoroethane, pentafluoroethane. 1,1,1,2-tetrafluoroethane and chlorotetrafluoroethane in the proportions shown in Table 2 were fed over the catalyst at a pressure of 12 barg and 380° C. The temperature was steadily increased to 500° C. off gas samples were taken and analysed by Gas Chromatography. The results are shown in Table 2.

TABLE 2

| SAMPLE | TEMP (° C.) | Org. Feed (g/min) | COMPOSITION (gc area %) | | | | |
|---|---|---|---|---|---|---|---|
| | | | 143a | 125 | 134a | 124 | ethane |
| Feed | — | — | 20.3 | 8.0 | 66.9 | 3.7 | 0.0 |
| Off Gas | 380 | 0.35 | 16.1 | 6.8 | 71.2 | 2.3 | 3.6 |

TABLE 2-continued

| SAMPLE | TEMP (° C.) | Org. Feed (g/min) | COMPOSITION (gc area %) | | | | |
|---|---|---|---|---|---|---|---|
| | | | 143a | 125 | 134a | 124 | ethane |
| Off Gas | 450 | 0.40 | 8.4 | 7.4 | 58.5 | 0.9 | 24.8 |
| Off Gas | 500 | 0.21 | 1.7 | 6.6 | 24.0 | 0.0 | 67.7 |

EXAMPLE 3

The procedure of Example 1 was followed except that the catalyst comprised 0.5% platinum supported on alumina and the mixed organic feed comprised 1,1,1-trifluoroethane, pentafluoroethane, 1,1,1,2-tetrafluoroethane and chlorotetrafluoroethane in the proportions shown in Table 3. The results are shown in Table 3.

TABLE 3

| SAMPLE | TEMP (° C.) | COMPOSITION (gc area %) | | | | |
|---|---|---|---|---|---|---|
| | | 143a | 125 | 134a | 115 | ethane/methane |
| Feed | — | 59.5 | 9.1 | 30.7 | 0.1 | 0.0 |
| Off Gas | 400 | 2.0 | 7.2 | 10.1 | 0.0 | 80.7 |

EXAMPLE 4

87 ml of a catalyst comprising 1.0% palladium supported on alumina was charged to a one inch diameter Monel reactor tube, the tube was placed in an oven and the catalyst was dried by heating to 250° C. in a stream of nitrogen (100 ml/minute) for 15 hours.

The nitrogen flow rate was increased at 300 ml/minute and a stream of hydrogen was passed over the catalyst at a flow rate of 120 ml/minutes. A mixed organic feed stream comprising 1,1,1-trifluoroethane and pentafluoroethane in the proportions shown in Table 4 was passed over the catalyst with a flow rate of 30 ml/minute at a temperature of 370° C. and atmospheric pressure. The temperature was varied, the off gases were sampled analysed by gas chromatography and the results are shown in Table 4.

TABLE 4

| SAMPLE | TEMP (° C.) | COMPOSITION (gc area %) | | |
|---|---|---|---|---|
| | | 143a | 125 | ethane/methane |
| Feed | — | 67.2 | 32.7 | 0.0 |
| Off Gas | 370 | 0.92 | 36.9 | 62.1 |
| Off Gas | 388 | 0.22 | 36.9 | 62.8 |
| Off Gas | 404 | 0.01 | 37.1 | 62.9 |

EXAMPLE 5

The procedure of Example 4 was repeated except that the catalyst comprised 0.5% platinum supported on alumina and the mixed organic feed comprised 1,1,1-trifluoroethane, pentafluoroethane, 1,1,1,2-tetrafluoroethane and chloropentafluoroethane in the proportions shown in Table 5. The results are also shown in Table 5.

TABLE 5

| SAMPLE | TEMP (° C.) | COMPOSITION (gc are %) | | | | ethane/methane |
|---|---|---|---|---|---|---|
| | | 143a | 123 | 134a | 125 | |
| Feed | — | 59.5 | 9.1 | 30.7 | 0.1 | 0.0 |
| Off Gas | 380 | 2.0 | 7.2 | 10.1 | 0.0 | 80.7 |
| Off Gas | 450 | 0.0 | 4.3 | 0.0 | 0.0 | 95.7 |

EXAMPLE 6

The procedure of Example 5 was repeated except that the catalyst comprised 16.0% nickel supported on alumina, the ratio of hydrogen to organic feed, and the temperature were varied, the off gases were sampled and analysed by gas chromatography and the results are shown in Table 6.

TABLE 6

| SAMPLE | TEMP (° C.) | $H_2$/Org Ratio | COMPOSITION (gc area %) | | | | ethane/methane |
|---|---|---|---|---|---|---|---|
| | | | 143a | 125 | 134a | 115 | |
| Feed | — | — | 57.6 | 8.8 | 33.2 | 0.1 | 0.0 |
| Off Gas | 450 | 5:1 | 0.0 | 11.5 | 5.4 | 0.0 | 62.7 |
| Off Gas | 400 | 8:1 | 0.0 | 11.5 | 25.7 | 0.0 | 57.3 |
| Off Gas | 450 | 8:1 | 0.0 | 7.4 | 0.0 | 0.0 | 92.6 |

EXAMPLE 7

57 g of a catalyst comprising 16% nickel oxide supported on alumina was charged to ¾"diameter Inconel reactor pipe and the reactor was placed in an oven. Hydrogen was passed over the catalyst, and a mixed organic feed stream comprising 1,1,1-trifluoroethane, pantafluoroethane and 1,1,1,2-tetrafluoroethane in the proportion shown in Table 4 was passed over the catalyst at 12 Barg pressure and at increasing elevated temperatures. The off gases from the reactor were periodically sampled and analysed by gas chromatography. The results are shown in Table 7.

TABLE 7

| SAMPLE | TEMP (° C.) | FLOW RATE (g/min) Organics | COMPOSITION (gc/area %) | | | | ethane/methane |
|---|---|---|---|---|---|---|---|
| | | | $H_2$ | 143a | 125 | 134a | |
| Feed | — | — | — | 14.3 | 6.2 | 79.4 | — |
| Off Gas | 298 | 0.65 | 0.42 | 10.4 | 6.1 | 83.4 | 0.0 |
| Off Gas | 477 | 0.73 | 0.57 | 0.0 | 6.9 | 8.3 | 84.8 |
| Off Gas | 511 | 0.40 | 0.71 | 0.0 | 7.2 | 3.1 | 89.7 |

143a = 1,1,1-trifluoroethane
125 = pentafluoroethane
134a = 1,1,1,2-tetrafluoroethane
124 = chlorotetrafluoroethane
115 = chloropentafluoroethane

What is claimed is:

1. A process for the removal of at least one compound selected from the group consisitng of chloroalkane, chlorofluoroalkane, hydrochlorofluoroalkane and hydrofluoroalkane impurities from pentafluoroethane which comprises contacting the impure pentafluoroethane with hydrogen at a temperature of at least 350° C. in the presence of a hydrogenation catalyst to convert the impurity or impurities to at least one member of the group consisting of a hydrofluoroalkane and a hydrocarbon and separating the resulting hydrofluoroalkane and/or hydrocarbon from the pentafluoroethane.

2. A process as claimed in claim 1 wherein the impure pentafluoroethane comprises a major proportion of pentafluoroethane.

3. A process as claimed in claim 1 or claim 2 wherein the catalyst comprises a Group VIII a metal.

4. A process as claimed in claim 3 wherein the catalyst is carried on a support comprising alumina or carbon.

5. A process as claimed in claim 1 wherein the elevated temperature is up to 600° C.

6. A process as claimed in claim 1 wherein the impure pentafluoroethane is contacted with hydrogen under superatmospheric pressure.

7. A process as claimed in claim 1 wherein the hydrogen is present in stoichiometric excess based on the impurity or impurities to be hydrogenated.

8. A process as claimed in claim 1 wherein the impure pentafluoroethane contains chloropentafluoroethane and is the product of hydrogenation of chloropentafluoroethane.

* * * * *